United States Patent [19]

Reiss et al.

[11] Patent Number: 5,916,166
[45] Date of Patent: Jun. 29, 1999

[54] MEDICAL GUIDEWIRE WITH FULLY HARDENED CORE

[75] Inventors: Robert E. Reiss, La Jolla; Gary W. Gomringer, La Mesa, both of Calif.

[73] Assignee: Interventional Technologies, Inc., San Diego, Calif.

[21] Appl. No.: 08/752,714

[22] Filed: Nov. 19, 1996

[51] Int. Cl.⁶ .............................. A61B 6/00; A61M 25/00
[52] U.S. Cl. ............................................ 600/434; 600/585
[58] Field of Search ...................................... 600/434, 585, 600/462, 550; 604/95, 280, 281, 282, 283

[56] References Cited

U.S. PATENT DOCUMENTS

| | | |
|---|---|---|
| Re. 33,911 | 5/1992 | Samson et al. . |
| 4,215,703 | 8/1980 | Willson . |
| 4,283,233 | 8/1981 | Goldstein . |
| 4,538,622 | 9/1985 | Samson et al. . |
| 4,554,929 | 11/1985 | Samson et al. . |
| 4,619,274 | 10/1986 | Morrison . |
| 4,721,117 | 1/1988 | Mar et al. . |
| 4,925,445 | 5/1990 | Hidetoshi et al. . |
| 4,984,581 | 1/1991 | Stice . |
| 5,069,226 | 12/1991 | Yamauchi . |
| 5,087,415 | 2/1992 | Hemphill . |

OTHER PUBLICATIONS

Marks, Standard Handbook for Mechanical Engineers, 8th edit., 1978, McGraw–Hill, 6–19 to 6–22 and 6–36 to 6–38.
Unterweiser, Heat Treater's Guide, Std. Practices and Proc. for Steel, 1982, Amer. Soc. Metals, 421–439.
Rosato, Designing with Plastics and Composites, 1991 Van Nostrand Reinhold 136–141.
Blake, Practical Stress Analysis in Engineering Design 1982, Marcel Dekker Inc. 46–47.
Peckner, Handbook of Stainless Steels, 1977, McGraw–Hill, 6–1 to 6–23 and 42–1 to 42–10.
Grosvenor, Basic Metallurgy, 1954, American Society for Metals, 150–151, 400–408.
Dove, Steel Wire Handbook, 1982, vol. 2, The Wire Association, Inc. 286, 301.

*Primary Examiner*—Richard J. Apley
*Assistant Examiner*—Justine R. Yu
*Attorney, Agent, or Firm*—Michael Klicpera, Esq.

[57] ABSTRACT

Guidewire comprising an elongated core element manufactured from a martensitic alloy that is heat-treated to render a fully hardened core throughout its cross sectional area. The core has a constant taper or step-down decreasing cross sectional area in a direction towards the distal end which is fully hardened throughout its longitudinal length. A single coil, or two coils are carried by and secured to said core element near the distal end.

22 Claims, 5 Drawing Sheets

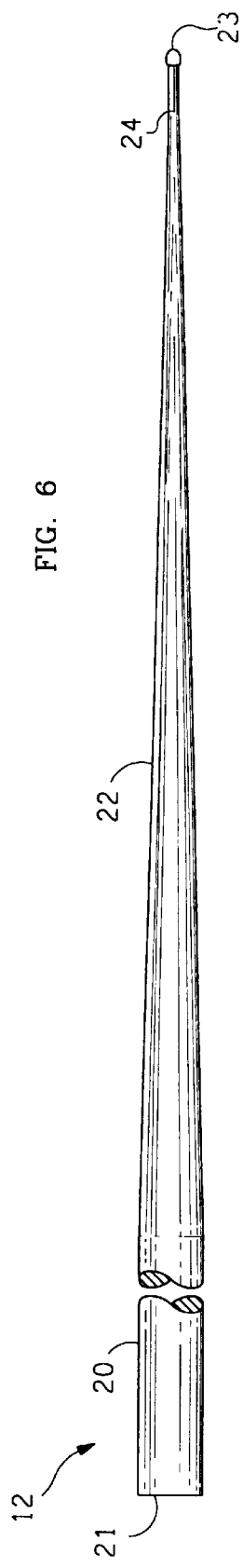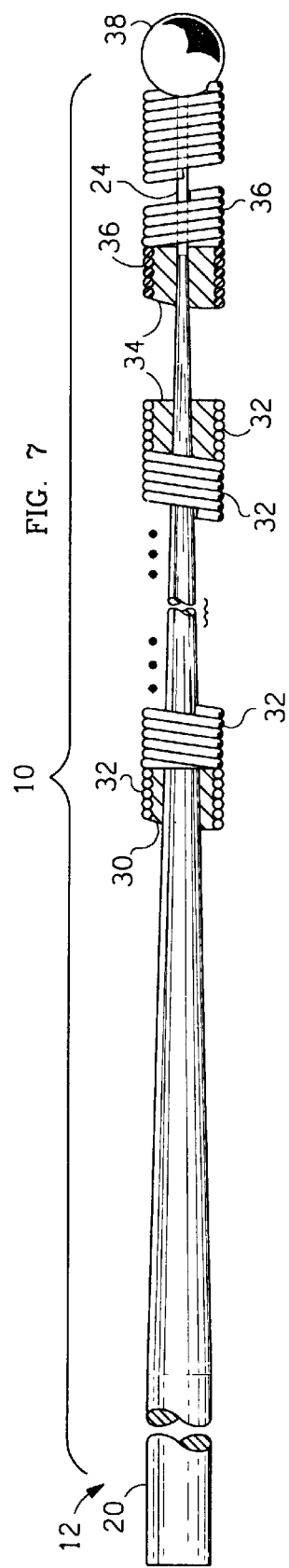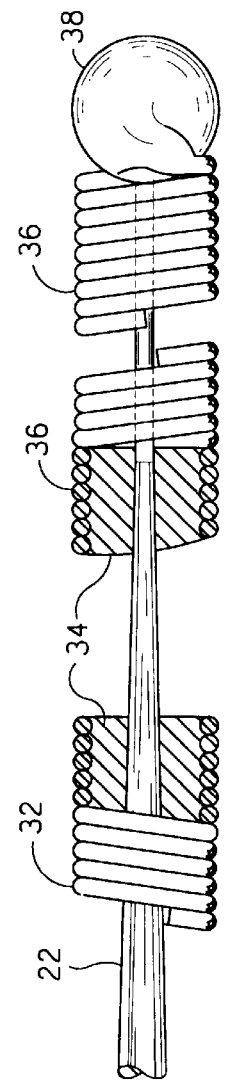
FIG. 6
FIG. 7
FIG. 8

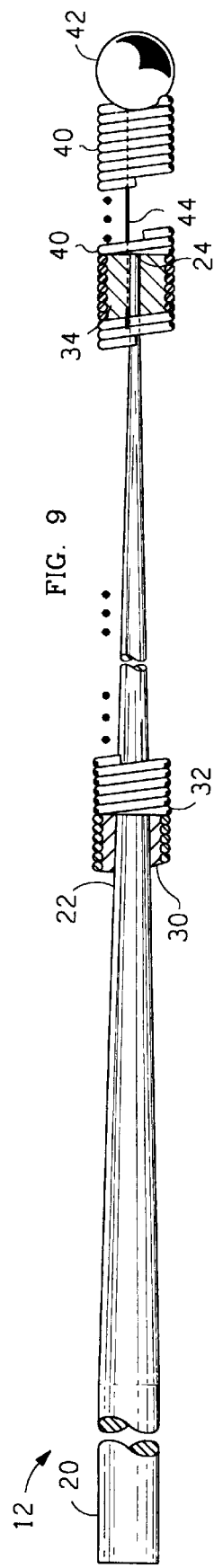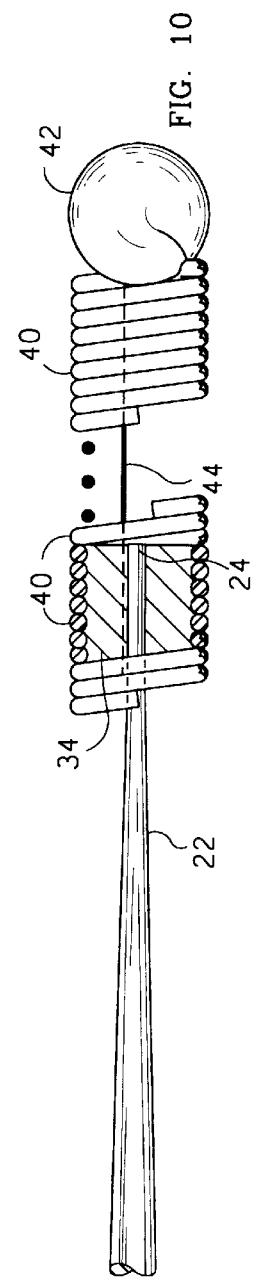

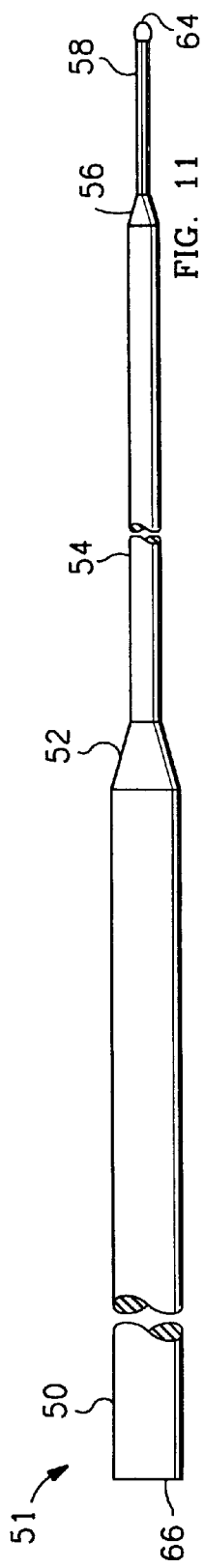
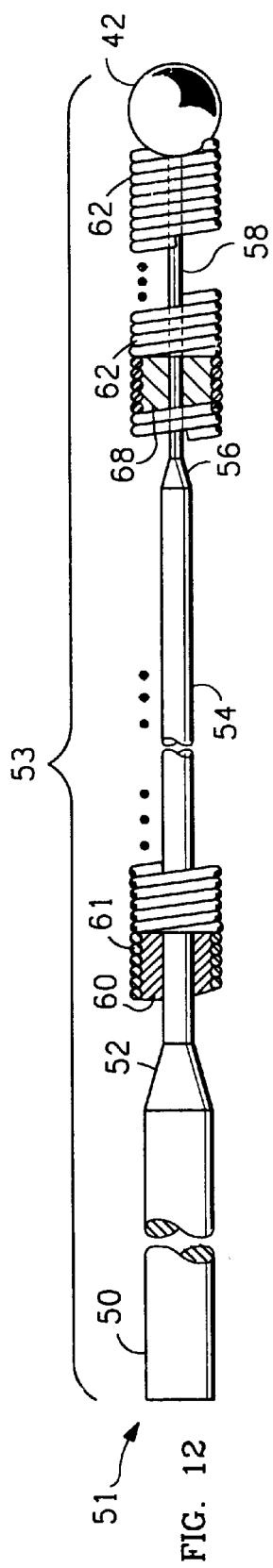
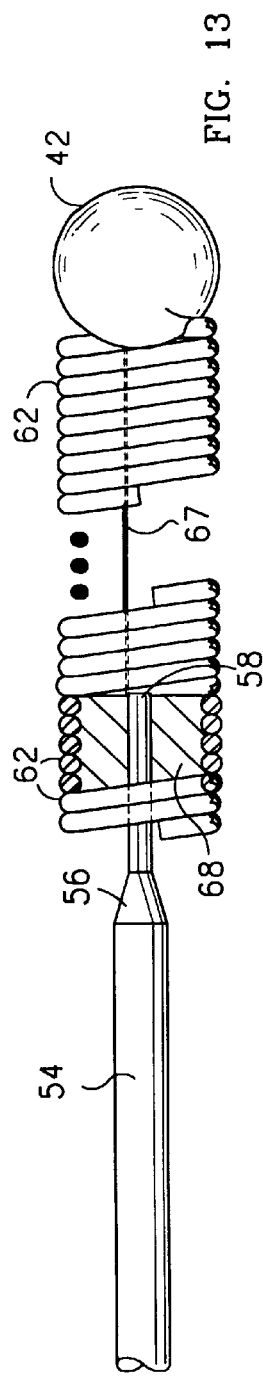

MEDICAL GUIDEWIRE WITH FULLY HARDENED CORE

FIELD OF THE INVENTION

This invention relates to guidewires for use with interventional and diagnostic catheters and more particularly, to guidewires with a fully hardened core having the characteristic of superior torsional control or torque transmission.

BACKGROUND OF THE INVENTION

Guidewires have long been used to facilitate diagnostic and therapeutic medical procedures. Generally speaking, a guidewire is the initial member inserted into a body cavity during many transluminal procedures. A guidewire is an elongated fine wire device intended to readily pass through body passageways to a location at which a medical procedure or treatment is to take place. Thereafter, in a typical arrangement, a catheter is threaded over the thus inserted guidewire, with the catheter following the pathway defined by the guidewire. In general terms, a guidewire is flexible, at least at its remote distal end tip.

Remote distal end tip flexibility is often enhanced by providing one or more fine coils at the distal portion of the guidewire and securing these coils to the distal end of the guidewire's core. Typically, this securement application also includes a rounded distal tip that imparts some atraumatic characteristics to the guidewire. In the usual approach, these components are secured together by soldering, brazing, welding or by using an adhesive such as ultraviolet-curing adhesives, catalytic-curing such as epoxy or anaerobic adhesives such as cyanoacrylate adhesives.

Distally tapered guidewires are generally composed of a stainless steel or austenitic metallic core which is not amendable to heat treatment for hardening the base metal. Stainless steel alloys employed in the medical field generally have a high chromium and low carbon content to provide resistance to oxidation and corrosion. Stainless steel or austenitic alloy guidewires are amendable to work hardening but the final process yields a wire that is hardened primarily in the outer layers. Any hardness developed by the work process decreases or is totally absent as the center of the core is approached where it remains relatively soft. After stainless steel or austenitic alloy guidewire cores are work hardened, they are distally tapered by standard diameter reduction processes, which exposes the relatively soft inner cross sectional layers and becomes the entire core of the distal end. This results in the stainless steel guidewire having inherently disportionate hardening throughout the length of the wire yielding suboptimal torsional characteristics. Inconsistent proximal to distal rotational movement makes it difficult for the clinician to penetrate small blood vessels while inadequate hardness affects the guidewire's catheter tracking capabilities. Stainless steel guidewires that suffer from inadequate entire cross sectional area hardening do not have high torsional capabilities for allowing the navigation through tortuous coronary, kidney or neurological vessels. In addition, such guidewires can suffer from snap or have unpredictable final tip positioning. Furthermore, it is important for a guidewire to be able to conform over sever curves and sharp angles without causing plastic deformation thereby having high ductility.

Therefore, there is a need for a torsionally strong, fully hardened, high ductility guidewire.

SUMMARY

The present invention employs martensitic alloys which are amendable to heat treatment that renders the core of a guidewire to become fully hardened throughout its entire cross sectional area. When this invention is tapered distally, the reduced diameter maintains the fully hardened characteristics rendering a guidewire that has a fully hardened core or mandrel from the proximal end throughout its longitudinal length to the distal tip. One advantage of this fully hardened, distally tapered, guidewire is that the relative torsion input generated at the proximal end is transmitted along the longitudinal length with the torsion output at the distal end virtually identical to the input. This is a desirable characteristic for a guidewire because it allows the clinician to predict the amount of distal tip rotation based on proximal torsional input while confirming the progress of this activity using a two dimensional fluoroscopy system.

Furthermore, it is important for a guidewire to have high ductility thereby allow it to conform over tortuous curves and sharp angles without causing plastic deformation. This can be demonstrated on a standard stress-strain curve, where the characteristics of elasticity and plasticity usually result in a bilinear curve, with one line representing the elastic response and the other the plastic response, and the bend between the two lines the yield point at which further stress results in deformation of the material. However, it is known that light steel alloys do not exhibit a clearly defined yield point. In such cases the yield strength is approximated by an offset method. Here, the yield strength is generally assumed to be that stress at which the material exhibits a permanent set of some constant value, such as 0.2% It has been demonstrated that the present invention exhibits a yield strength where the constant value at which a permanent set develops is substantially lower than 0.2%. Furthermore, in all standard stainless steel and austenitic alloy guidewires manufactured to date, the elasticity portion of the stress-strain curve is lower than that for the present invention at any given wire diameter. Therefore, the present invention has a significant advantage in that the yield strength is higher than the standard guidewire thereby having higher ductility for a given cross sectional area. These parameters translate into a guidewire which provides the clinician with a both a safer and higher performance design (e.g., ductility, catheter support, one-to-one torsion tranmission) then presently available.

In general, it is an object of the present invention to provide a guidewire that is fully hardened throughout its cross sectional area.

Another object of the invention is to provide a guidewire of the above character that has high and consistent torsional capabilities.

Another object of the present invention is to provide a guidewire manufactured from a high ductility material thereby providing superior resistance to deformation when stressed over that of standard stainless steed guidewires.

Another object of the present invention is to provide a guide wire of the above character which is provided with a small tip facilitating deep penetration into small vessels.

Another object of the present invention is to provide a guide wire of the above character which has a relatively large proximal diameter to facilitate tracking of the catheter while it is in use.

Another object of the present invention is to provide a guide wire of the above character that has a very floppy distal end.

Another object of the present invention is to provide a guide wire of the above character that can be provided with various degrees of floppiness on its distal end.

Additional objects and features of the invention will appear from the following description in which the preferred embodiment is set forth in detail in conjunction with the accompanying drawings.

BRIEF DESCRIPTION OF THE DRAWINGS

FIG. 6 is a side elevational view of the constant tapered core wire used in connection with construction of the fully hardened guidewire incorporating the present invention.

FIG. 7 is a side elevational view partially in cross section of a constant tapered guide wire incorporating the present invention which is provided with a floppy distal end having an attached round protrusion.

FIG. 8 is an enlarged view of the distal extremity of the guide wire shown in FIG. 7.

FIG. 9 is a side elevational view partially in cross section of a constant tapered guide wire incorporating the present invention which is provided with a floppy distal end having a detached round protrusion and safety wire.

FIG. 10 is an enlarged view of the distal extremity of the guide wire shown in FIG. 9.

FIG. 11 is a side elevational view of the step down tapered core wire used in connection with construction of the fully hardened guidewire incorporating the present invention.

FIG. 12 is a side elevational view partially in cross section of a step down tapered guide wire incorporating the present invention which is provided with a floppy distal end having an attached round protrusion.

FIG. 13 is a side elevational view partially in cross section of a step down tapered guide wire incorporating the present invention which is provided with a floppy distal end having a detached round protrusion and safety wire.

DESCRIPTION OF THE PREFERRED EMBODIMENTS

In general, the torsional guidewire with a fully hardened core comprises an elongate core element having proximal and distal ends and having a decreasing cross sectional area in a direction toward the distal end. It is also comprised of one or more coils carried by and secured to the core element and extending over the distal extremity of the core element. The coil is formed of wire that is wound in a coil or helix configuration.

Figure 1:
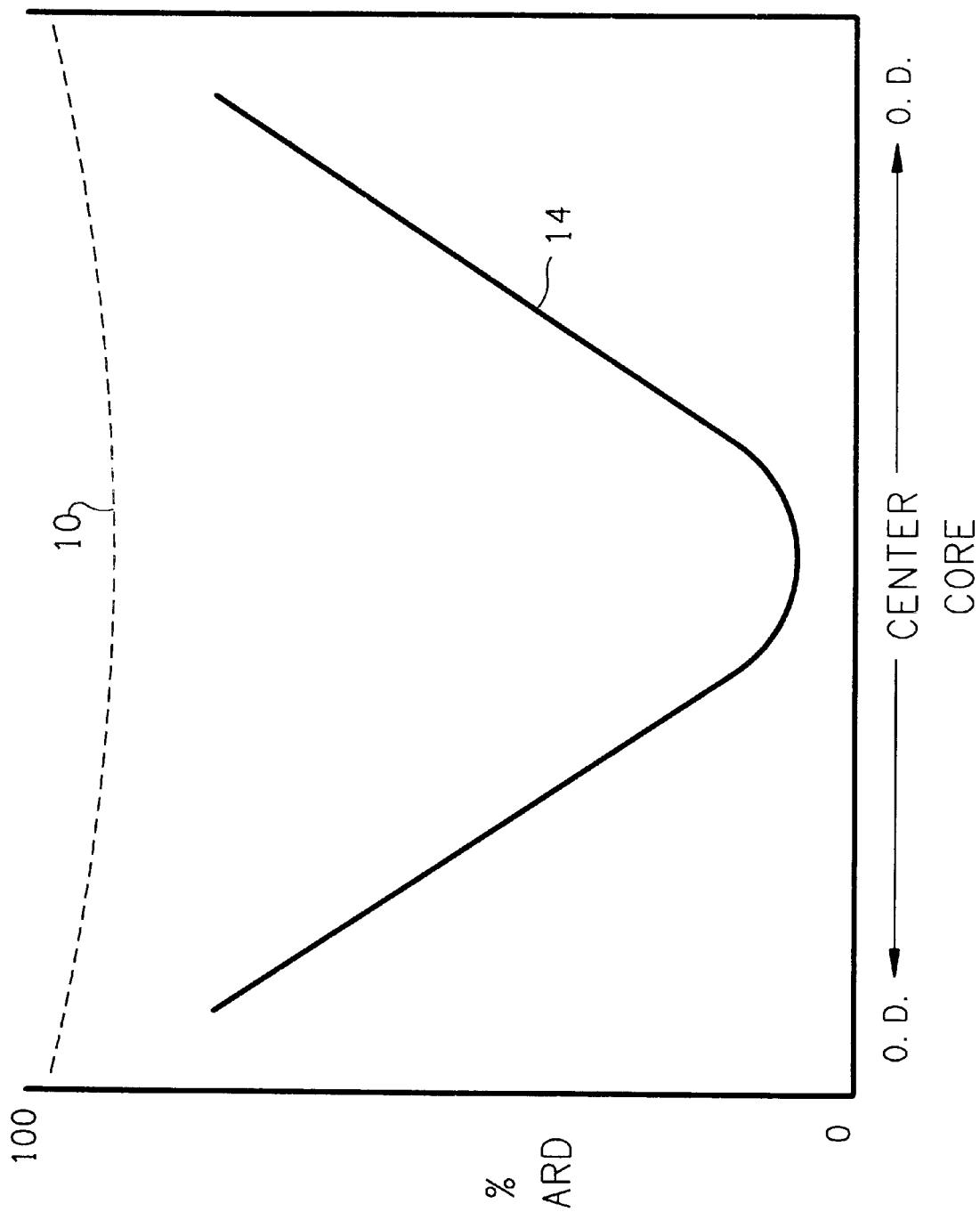
FIG. 1 is a graphical depiction of the relative percent hardness throughout the cross sectional area of the core comparing that of a standard stainless steel with that of the present invention.

In FIG. 1, a graph depicts the relative percent hardness throughout the entire cross sectional area of a guidewire core or mandrel comparing a standard stainless steel guidewire 14 with the present invention 10. This graph represents a cross section of each wire diameter before either has been subjected to any tapering process. As the graph demonstrates, when the stainless steel guidewire's 14 diameter is tapered, the reduced cross section portions become relatively less hard as the center of the cross section is approached. Conversely, when the present invention guidewire core is tapered, the reduced cross section maintains the hardness throughout the length of the guidewire. Furthermore, the present invention employs a material that has a higher ductility and yield strength for a given wire diameter, and can be fully hardened throughout it cross section by heat-treatment.

Figure 2:
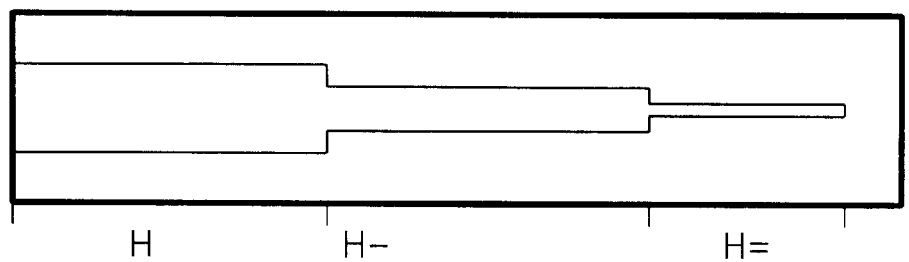
FIG. 2 is a graphical representation of the relative degree of hardness along the entire length of a standard stainless steel guidewire with a step-down tapered core.
Figure 3:
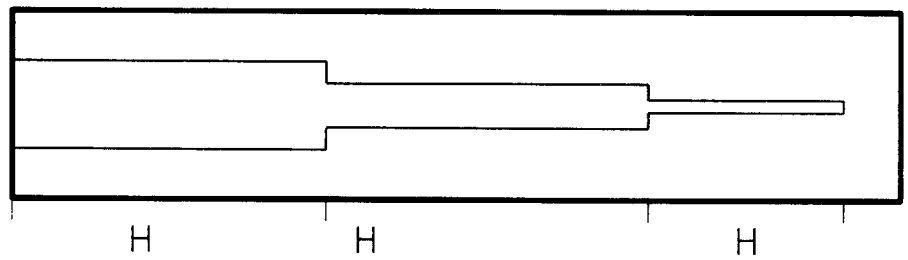
FIG. 3 is a graphical representation of the relative degree of hardness along the entire length of the present invention with a step-down tapered core.

As shown more particularly in FIG. 2 the step-down diameter of the standard stainless steel or austenitic alloy guidewire core yields a decreasing hardness (represented in relative decreasing hardness hereinafter by the marks H, H– and H=) as the softer core is exposed. Conversely, as shown in FIG. 3, the heat treated, fully hard core of the present invention maintains a constant hardness (H) throughout its longitudinal length regardless that the surface layers are removed during tapering processing to expose inner material.

Figure 4:
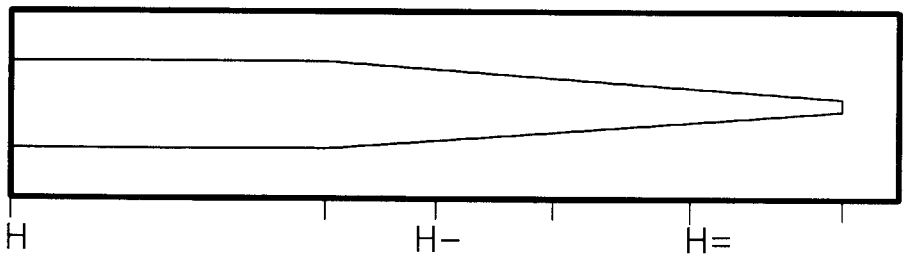
FIG. 4 is a graphical representation of the relative degree of hardness along the entire length of a standard stainless steel guidewire with a constant tapered core.
Figure 5:
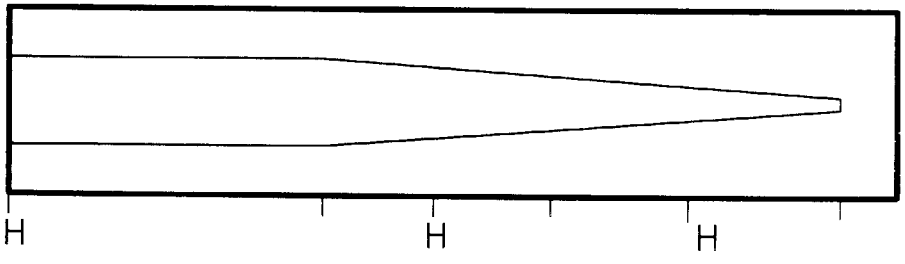
FIG. 5 is a graphical representation of the relative degree of hardness along the entire length of the present invention with a constant tapered core.

Additionally, as shown more particularly in FIG. 4 the constant taper diameter of the standard stainless steel or austenitic alloy guidewire core yields a decreasing hardness (H, H–, and H=) as the softer core is exposed. Conversely, as shown in FIG. 5, the heat treated, fully hard core of the present inventions maintains a constant hardness (H) throughout its longitudinal length regardless that the surface layers are removed during tapering processing to expose the inner core.

The core element 12, shown in more detail in FIG. 6, is formed of a suitable material such as one of the martensitic steel alloys. The herein described advantages of the present invention are achieved in an age or temperature hardened, martensitic steel alloy as summarized in Table I below, containing in weight percent, about:

TABLE I

|    | Broad      | Intermediate | Preferred  |
|----|------------|--------------|------------|
| C  | 0.20–0.33  | 0.20–0.31    | 0.21–0.27  |
| Cr | 2.0–4.0    | 2.25–3.50    | 2.5–3.3    |
| Ni | 10.5–15.0  | 10.75–13.50  | 11.0–12.0  |
| Mo | 0.75–1.75  | 0.75–1.5     | 1.0–1.3    |
| Co | 8–17       | 10–15        | 11–14      |
| Fe | balance    | balance      | balance    |

Here and throughout, the described advantages of the present invention are also achieved in further age or temperature hardened, martensitic steel alloys, as summarized in Table II below, containing in weight percent, about:

TABLE II

|            | wt. %       |
|------------|-------------|
| Carbon     | 0.10–1.20   |
| Manganese  | 1.00–1.25   |
| Chromium   | 4.00–18.00  |
| Silicone   | 0.50–1.00   |
| Nickel     | 0.00–2.50   |
| Molybdenum | 0.00–0.75   |
| Iron       | balance     |

The foregoing tabluations are provided as a convenient summary and is not intended to restrict the lower and upper values of the ranges of the individual elements of the present invention.

Also shown is the proximal portion 20 with a relatively constant diameter throughout its entire length, a constant taper 22 and distal end portion 24. The core element 12 has a suitable diameter ranging from 0.008 to 0.0199 inches and has a suitable length ranging from 100 to 300 centimeters. The core element 12 is provided with proximal and distal ends 21 and 23, respectively. The core element 12 is ground to provide a core wire that has a decreasing cross sectional area 22 in a direction toward the distal end. Although not shown to scale, the core 12 is provided with a cylindrical proximal portion 20 that extends over most of the length of the core. A tapered portion 22 adjoins the proximal portion 20 and extends over a suitable distance ranging from 2 to 20 inches, with a preferred range of 4 to 15 inches. The remaining length of the core element 12 is ground to a distal diameter ranging from 0.002 to 0.004 inches for a length of approximately 2 to 5 centimeters.

Thus it is shown that the core element 12 has been carefully dimensioned by grinding to provide a decreasing cross sectional area or a taper as hereinbefore described.

As shown in FIG. 7, guidewire 10 may consist of one or two coils (36 and alternately 32) surrounding the core and attached near the distal end. Distal coil 36 itself is shown in FIGS. 7 and 8 and is an important component of the guidewire 10. Distal coil 32 functions to protect the small diameter distal section 24 of guidewire 10 from damage and maintain its floppy characteristics. Coil 36 is wound from a suitable material such as gold/nickel alloy and has a diameter that ranges from 0.001 to 0.004 inches with a preferable diameter of 0.003 inches.

As a skill artisan will appreciate, the material of coil 36 may also be selected from a wide range of metallic (e.g., gold, tantalum, tungsten, platinum, iridium, rhenium and alloys of the materials) or polymeric materials to meet a particular need.

A distal ball 38, as shown in FIG. 7, is formed on the distal end 23 of the core using a process that utilizes a portion of the distal coil 36 as material to form the ball 38 as hereinafter described.

Another core or coil section can be provided which is identified as proximal coil 32. As shown in FIG. 7, which details a dual coil design, the distal end of the proximal coil 32 abuts to the proximal end of distal coil 36. Proximal coil 32 surrounds the tapered core 22 near the distal end and functions to further protect the small diameter of the distal constant taper. The wire from which proximal coil 32 is wound is formed of a suitable material such as stainless steel alloy and has a diameter that ranges from 0.001 to 0.004 inches with a preferable diameter of 0.002 inches. As a skill artisan will appreciate, the material of coil 32 may also be selected from a wide range of other materials to meet a particular need.

Not shown in the drawings is an optional coating that can be applied to the outer surface of core 20, including a portion of the constant tapered section 22. This coating may consist of Teflon or PTFE material, Parylene, or other lubricous material.

Another embodiment of the present invention, as shown in FIG. 9 and 10, consists of a guidewire utilizing the components describe above, except that coil 40 extends a suitable distance beyond the distal extremity of the core element 24, for example, 0.40 to 0.80 inches beyond end 23, with a preferable range of 0.55 to 0.65 inches. A safety ribbon 44, formed of a suitable material such as tungsten or a tungsten alloy and of suitable dimension such as a width of 0.003 inches and a thickness of 0.001 inches, extends from the distal end of core 24 to the outermost or distal extremity of coil 40. The proximal extremity of the safety ribbon 44 and the proximal end of coil 40 are joined into a unitary assembly with the distal portion of core element 12 by a suitable means such as brazing, or soldering, or by using an adhesive 34. The braze, solder or adhesive joint is formed so that the material fills the interstices between coils 32 and 40.

The distal extremity of the coil 40 is provided with a suitable means for rounding of the extremity and securing the distal extremity of the safety wire or ribbon 44. It consists of a ball or plug 42 formed of a suitable material such as gold bonded onto or formed from the distal end of coil 40 and safety ribbon 44.

Alternatively, another coil section is provided which can be identified as the proximal coil 32. As shown in FIG. 9, which details a dual coil design, the distal end of the proximal coil 32 abuts to the proximal end of distal coil 40. Proximal coil 32 surrounds the tapered core portion 22 near the distal end and functions to further protect the small diameter of the distal constant taper. In this context, the ends of coils 40 and 32 are screwed or butted together and joined into a unitary assembly with core element 12 by the hereinbefore described means. The proximal portion of coil 32 is secured to the tapered core portion 22 by a suitable means such as brazing, soldering or adhesive means 30. The braze, solder or adhesive joint is formed so that the material fills the interstices between coils 32.

The solder, brazing or adhesive materials utilized in connection with the manufacture of the guidewire are of conventional types. For example, the solder can be a conventional silver alloy, or tin silver alloy whereas the brazing material can be an alloy of silver, copper, tin or nickel. The adhesive materials can be a catalyst-curing such as an epoxy, or ultraviolet-curing, or anaerobic adhesives such as cyanoacrylate.

In another embodiment of the present invention, step-down core element 51, shown in more detail in FIG. 11, is formed of a suitable material such as one of the martensitic steel alloys. The proximal core 50 has a suitable diameter ranging from 0.008 to 0.0199 inches and has a suitable length ranging from 100 to 300 centimeters. It is provided with a tapered portion 52 which adjoins one extremity of the proximal core 50 which adjoins another cylindrical intermediate portion 54 having a suitable dimension such as 0.005 to 0.010 inches in diameter and preferable diameter of approximately 0.008 inches. Another tapered portion 56 is provided which adjoins intermediate portion 54 with a distal portion 58. The distal portion 58 has a suitable dimension equal or less than 0.007 inches in diameter. As with the constant tapered core 12 described above, the step-down core 51 can have a suitable length of a range from 100 to 300 centimeters. Cylindrical intermediate portion 54 can have a length of approximately 15 to 30 centimeters and a preferable length of 27 centimeters. Distal portion 58 can have a length of approximately 4 centimeters. Tapered portions 52 and 56 can have a length of approximately 0.5 to 2.0 centimeters.

As described above for the constant taper core 12, the step-down core 51 can be fitted with a single or dual coils secured to the coil as hereinafter described and as shown in FIG. 12.

Furthermore, another embodiment is shown in FIG. 13, where coil 62 extends a suitable distance beyond the distal extremity of the step-down core element 58, as for example a length of 0.40 to 0.80 inches from the end 64 and preferably 0.60 inches plus or minus 0.005 inches. A safety ribbon 67, formed of a suitable material such as tungsten or a tungsten alloy and of suitable dimension such as a width of 0.003 inches and a thickness of 0.001 inches, extends from the distal extremity of the core portion 58 to the outermost or distal extremity of coil 62. The proximal extremity of the safety ribbon 67 and the end of coil 62 are joined into a unitary assembly with the core element 51 by a suitable means such as brazing, or soldering.

The distal extremity of the coil 62 is provided with a suitable means for rounding of the extremity and securing the distal extremity of the safety wire or ribbon 67. It consists of a ball or plug 42 formed of a suitable material such as gold bonded onto or formed from the distal end of coil 62 and safety ribbon 67.

With these fabricated components hereinbefore described, the guidewire may now be assembled. First, the base martensitic steel allow is drawn to a specified diameter, straighten and cut to length, and then age or heat-treated within a range of 700° F. to 1950° F., with a preferable temperature range of 720° F. to 900° F. To start the assembly, the core is ground to a specific tapered configuration. As described above, one embodiment uses a constant tapered core 12 and another embodiment uses a step-down core 51. Once the core is ground and appropriately cleaned, the proximal coil 32 or 62, if applicable, is threaded over the core 12 or 51, respectively. Then distal coil 36 or 40 is slid over the core wire and if applicable, the proximal and distal coils are abutted or screwed together. Hereinafter, the manufacturing process differs between the embodiments shown in FIGS. 7, 8 and 12 where the distal ball 38 or 42 is secured to the distal extremity of the distal portion 24 or 58 of the core, and the embodiments shown in FIGS. 9, 10, and 13 where the coil 40 or 62 extends a suitable distance beyond the distal extremity of the core element 24 or 58, and a safety ribbon 44 or 67 extends from the distal extremity of the core portion 24 or 58 to the outermost or distal extremity of coil 40 or 62, terminating in a distal ball.

In the embodiments where the distal ball 38 (constant taper) or 42 (step-down taper) is secured to the distal extremity of the core, the manufacturing process continues by inserting a distal coil 36 or 62 into a fixture/collet such that a distal end portion of the coil projects out of the collet and beyond its face, and locating the core 12 or 51 at a staged position remote from this face of the collet. Next, the projecting distal end portion of the coil is heated to form a heated tip mass until this mass engages the face of the collet. Upon cooling, the leading end is joined to the now solidified coil tip mass so as to define a distal ball 38 or 42 secured to the distal end of the core 24 or 58. This heated mass also secures the distal end of the core, the distal extremity of the coil, and the ball together forming a unitary assembly. After the distal ball is formed, the intermediate joint 32 or 68 is formed securing the proximal end of the distal coil and if applicable, the distal end of the proximal coil to the core. If the proximal coil is employed, then a proximal joint 30 or 60 is formed securing the proximal end of the proximal coil to the core.

Returning to the embodiments where the coil 40 or 62 extends a suitable distance beyond the distal extremity of core 24 or 58, and the safety ribbon 44 or 67 extends from the distal extremity of the core portion 24 or 58 to the outermost extremity of coil 40 or 62 and terminates in a spherical ball 38 or 42. The manufacturing process continues first by inserting the distal coil 36 or 62 into a collet with safety ribbon 44 or 67 projecting out of the collet and beyond its face, and locating safety ribbon 44 or 67 at a staged position remote from the face of the collet. Next, the projecting distal end portion of the coil and safety ribbon is heated to form a heated tip mass until this mass engages the face of the collet. Upon cooling, the leading end is joined to the now solidified coil tip mass so as to define a distal ball 38 or 42 secured to the distal end of the core 24 or 58. After the distal ball is formed, the intermediate joint 32 or 68 is formed securing the proximal end of the distal coil and if applicable, the distal end of the proximal coil to the core. If the proximal coil is employed, then a proximal joint 30 or 60 is formed securing the proximal end of the proximal coil to the core.

The operation and use of the guidewire 10 or 53 is very similar to that for other standard guidewires. It, however, has numerous characteristics that are superior to standard stainless steel or austenitic alloy guidewires.

It is apparent from the foregoing that there has been provided a new and improved guide wire that is fully hardened throughout its longitudinal length, and has superior torsional capabilities and ductility. The present invention also has a construction that can be economically manufactured in quantity with great precision.

What is claimed is:

1. A guidewire comprising:

an elongated flexible element formed from a martensitic alloy that is hardened throughout its cross sectional area by heat treatment that is consistently hardened throughout its cross sectional area by treatment with heat;

said elongated flexible element having a proximal portion ranging from 0.008 to 0.00199 inches in diameter;

a distal portion of less than 0.007 inches in diameter;

an intermediate section having a decreasing cross sectional area in a direction towards said distal portion; and a first coil having a proximal extremity and a distal extremity and secured to said distal portion.

2. A guidewire as recited in claim 1, further comprising a second coil having a proximal extremity and a distal extremity, said distal extremity of the second coil engaged and secured to the proximal extremity of the first coil and the proximal extremity of the second coil secured to said intermediate section.

3. A guidewire as recited in claim 1, wherein the distal extremity of said first coil extends beyond the distal portion of said elongated flexible element together with a safety wire secured to said distal extremity of said first coil and also secured to said elongated flexible element.

4. A guidewire as recited in claim 1, wherein said alloy consists essentially of, in weight percent, about

|  | wt. % |
|---|---|
| Carbon | 0.20–0.33 |
| Chromium | 2.0–4.0 |
| Nickel | 10.5–15.0 |
| Molybdenum | 0.75–1.75 |
| Cobalt | 8–17 | and the balance is essentially iron.

5. A guidewire as recited in claim 1, further comprising a second coil having a proximal extremity and a distal extremity, said distal extremity of the second coil engaged and secured to the proximal extremity of the first coil and the proximal extremity of the second coil secured to said intermediate section.

6. A guidewire as recited in claim 2, wherein said first coil is comprised of a gold nickel alloy, tungsten/ iridium alloy, or tungsten alloy and said second coil is comprised of stainless steel.

7. A guidewire as recited in claim 1, wherein said elongate flexible element has cylindrical portions of different diameters and tapered portions of different diameters adjoining said cylindrical portions.

8. A guidewire as recited in claim 1, wherein a distal extremity of said first coil extends beyond the distal portion of said elongated flexible element together with a safety wire secured to said distal extremity of said first coil and also secured to said elongated flexible element.

9. A guidewire as recited in claim 1, wherein the distal extremity of said first coil extends beyond the distal portion of said elongated flexible element together with a safety wire secured to said distal extremity of said first coil and also secured to said elongated flexible element.

10. A guidewire comprising:

an elongated flexible element formed from a martensitic steel alloy that is hardened throughout its cross sectional area by heat treatment;

said flexible element having a proximal portion ranging from 0.008 to 0.00199 inches in diameter;

distal portion of less than 0.007 inches in diameter;

and an intermediate section having a decreasing cross sectional area in a direction towards said distal portion; and a first coil having a proximal extremity and a distal extremity and secured to said distal portion.

11. A guidewire as recited in claim 10, further comprising a second coil having a proximal extremity and a distal extremity, said distal extremity of the second coil engaged and secured to the proximal extremity of the first coil and the proximal extremity of the second coil secured to said intermediate section.

12. A guidewire as recited in claim 10, wherein a distal extremity of said first coil extends beyond the distal portion of said elongated flexible element together with a safety wire secured to said distal extremity of said first coil and also secured to said elongated flexible element.

13. A guidewire as recited in claim 10, wherein said elongated flexible element has cylindrical portions of different diameters and tapered portions of different diameters adjoining said cylindrical portions.

14. A guidewire as recited in claim 10, wherein said elongated flexible element has a continuous tapered section having a proximal end and a distal end, said proximal end adjoining said proximal portion and said distal end adjoining said distal portion.

15. A guidewire as recited in claim 10, wherein said martensitic steel alloy consisting essentially of, in weight percent, about

|  | wt. % |
| --- | --- |
| Carbon | 0.10–1.20 |
| Manganese | 1.00–1.25 |
| Chromium | 4.00–18.00 |
| Silicone | 0.50–1.00 |
| Nickel | 0.00–2.50 |
| Molybdenum | 0.00–0.75 | and the balance is essentially iron.

16. A guidewire comprising:

an elongated core element made from a martensitic steel alloy that is hardened throughout its cross sectional area by heat treatment, said elongated core element having a proximal portion and distal portion;

an first coil formed of a radiopaque material having a proximal end and a distal end; and a second coil carried by, surrounding and secured to said core element, said coil having proximal and distal ends.

17. A guidewire as recited in claim 16, wherein said second coil has a substantially uniform diameter together with a rounded tip carried by the distal end of the second coil.

18. A guidewire as in claim 16, wherein said second coil has proximal and distal ends engaged to the core element and has said distal end juxtaposed to the proximal end of the first coil and a bond affixing the distal and proximal ends of the first coil and the distal and proximal ends of the second coil to the core element.

19. A guidewire as in claim 16, wherein said elongated core element has cylindrical portions of different diameters and tapered portions of different diameters adjoining said cylindrical portions.

20. A guidewire as recited in claim 16, wherein said elongated core element has a continuous tapered section having a proximal end and a distal end, said proximal end adjoining said proximal portion and said distal end adjoining said distal portion.

21. A guidewire comprising an flexible elongate martensitic steel alloy element said elongated element is consistently hardened throughout its cross sectional area by heat treatment, a coil carried by said flexible elongate martensitic steel alloy element, said coil being formed of first and second sections, said first and said second sections having end portions adjoining each other and means forming a bond between the ends of said first and second sections and a portion of said flexible elongate martensitic steel alloy element, and a rounded protrusion carried by the distal extremity of the coil.

22. A guide wire as recited in claim 21, further comprising a safety wire extending from the flexible elongate martensitic steel alloy element and bonded to said rounded protrusion.

* * * * *

UNITED STATES PATENT AND TRADEMARK OFFICE
CERTIFICATE OF CORRECTION

PATENT NO. : 5,916,166
DATED : Jun. 29, 1999
INVENTOR(S) : Reiss et al.

It is certified that error appears in the above-identified patent and that said Letters Patent is hereby corrected as shown below:

Column 2, line 27, insert a period between the words "0.2% It"
Column 2, line 51, replace the word "steed" with "steel"
Column 4, line 8, replace the word "it" with "its"
Column 5, line 57, replace the word "describe" with "described"
Column 7, line 13, replace the word "straighten" with "straightened"
Column 8, Claim 1, line 3, delete "that is hardened throughout its cross sectional"
Column 8, Claim 1, line 4, delete "area by heat treatment"
Column 9, Claim 10, line 5, replace "0.00199" with "0.0199"

Signed and Sealed this

Twenty-eighth Day of December, 1999

Attest:

Q. TODD DICKINSON

Attesting Officer

Acting Commissioner of Patents and Trademarks